(12) United States Patent
Dubac et al.

(10) Patent No.: US 6,455,738 B1
(45) Date of Patent: Sep. 24, 2002

(54) PROCESS FOR THE SULFONATION OF AN AROMATIC COMPOUND

(75) Inventors: Jacques Dubac, Pechbusque; Christophe Le Roux, Chateauroux; Sigrid Repichet, Fumel, all of (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/615,537

(22) Filed: Jul. 13, 2000

(51) Int. Cl.$^7$ .............................................. C07C 315/00
(52) U.S. Cl. ........................................... 568/28; 568/34
(58) Field of Search ............................. 568/28, 30, 31, 568/32, 33, 34

(56) References Cited

U.S. PATENT DOCUMENTS

| | | | | |
|---|---|---|---|---|
| 2,768,211 A | * | 10/1956 | Towne et al. | |
| 2,781,402 A | * | 2/1957 | Chadwick et al. | |
| 2,999,883 A | * | 9/1961 | Schoot et al. | |
| 3,060,193 A | * | 10/1962 | Schoot et al. | |
| 3,334,146 A | * | 8/1967 | Pitt et al. | |
| 3,402,204 A | * | 9/1968 | Plummer et al. | |
| 3,729,517 A | * | 4/1973 | Bracke et al. | |
| 3,891,713 A | * | 6/1975 | Farona et al. | |
| 4,172,852 A | * | 10/1979 | Ark et al. | |
| 4,414,406 A | * | 11/1983 | Fields | 560/109 |
| 4,778,932 A | * | 10/1988 | Manami et al. | 568/33 |
| 4,876,390 A | * | 10/1989 | McCulloch | 568/34 |
| 4,950,793 A | * | 8/1990 | Souma | 568/34 |
| 4,983,773 A | * | 1/1991 | Stumpp et al. | 568/34 |
| 6,184,418 B1 | * | 2/2001 | Dubac et al. | 568/319 |

OTHER PUBLICATIONS

CA:83:496734 abs of JP50053345 May 12, 1975.*
"Tetrahedron Letters 40 (1999) 9233–9234".

* cited by examiner

Primary Examiner—Jean F. Vollano

(57) ABSTRACT

A subject-matter of the present invention is a process for the sulfonation of an activated or deactivated aromatic compound. The invention applies to the preparation of aromatic sulfones. The process for the sulfonation of an aromatic compound according to the invention comprises the reaction of said aromatic compound with a sulfonating agent, in particular an aryl or alkyl sulfonating agent, in the presence of a catalytically effective amount of a mixture of a bismuth trihalide and of perfluoroalkanesulfonic acid.

22 Claims, No Drawings

PROCESS FOR THE SULFONATION OF AN AROMATIC COMPOUND

A subject-matter of the present invention is a novel catalytic composition and its use as Lewis acid, in particular in reacting an acid anhydride or halide with an aromatic derivative, for example an acylation. This use is particularly advantageous in sulfonation processes, sometimes denoted by sulfonylation processes, is which consists in grafting an —$SO_2$-Grp radical. This process is targeted in particular at a process for the sulfonation of an aromatic compound. More specifically, the invention relates to a process for the sulfonation of an activated or deactivated aromatic compound. Grp means here the organic part of the sulfonyl radical; it represents a carbonaceous group, in particular a fluorocarbonaceous group, advantageously a hydrocarbonaceous group, that is to say comprising hydrogen and carbon, chosen more particularly from aryls or alkyls.

In the account which follows of the present invention, the term "aromatic compound" is understood to mean the conventional notion of aromaticity as defined in the literature, particularly by Jerry March, Advanced Organic Chemistry, 4th edition, John Wiley and Sons, 1992, pp. 40 et seq.

The term "deactivated aromatic compound" defines a substituent-free aromatic compound, such as, for example, benzene, or an aromatic compound comprising one or more substituents which deactivate the aromatic nucleus, such as electron-withdrawing groups.

The term "activated aromatic compound" denotes an aromatic compound comprising one or more substituents which activate the aromatic nucleus, such as electron-donating groups.

The notions of electron-withdrawing groups and electron-donating groups are defined in the literature. Reference may be made, inter alia, to the work by Jerry March, Advanced Organic Chemistry, 4th edition, John Wiley and Sons, 1992, Chapter 9, pp. 273–292.

A conventional process for the preparation of of aromatic sulfones consists in carrying out a sulfonation reaction of Friedel-Crafts type.

The aromatic compound and an aryl sulfonating agent are reacted in the presence of a catalyst, which is generally aluminum chloride.

However, the use of aluminum chloride exhibits numerous disadvantages. Aluminum chloride is a corrosive and irritating product. Furthermore, it is necessary to employ a large amount of aluminum chloride at least equal to stoichiometry, as a result of the complexing of the sulfone formed. Consequently, aluminum chloride is thus not a true catalyst. In addition, at the end of the reaction, it is necessary to remove the aluminum chloride from the reaction mixture by carrying out an acidic or basic hydrolysis.

This hydrolysis technique involves the addition of water to the reaction mixture, which significantly complicates the implementation of the process as the metal cation, and more particularly the aluminum cation, then forms, in the presence of water, polyoxy- and/or polyhydroxo-aluminum complexes with a milky consistency which are difficult to separate subsequently. This results in the need to carry out a lengthy and expensive treatment comprising, after the hydrolysis, extraction of the organic phase, separation of the aqueous and organic phases, indeed drying of the latter. The separation of the aluminum chloride is thus lengthy and expensive. Furthermore, the problem is posed of the saline aqueous effluents which subsequently have to be neutralized, which requires an additional operation. Furthermore, the aluminum chloride cannot be recycled because of its hydrolysis.

The use of bismuth tritriflates [$(TfO)_3Bi$; TfO meaning: $CF_3SO_2$—] as Lewis acid has also been provided but these compounds are both very expensive, in particular because of the cost of the triflic anion, and very difficult to manufacture. The patent application filed on behalf of the Applicant Company, published under No. EPA 0 877 726, illustrates these difficulties.

One of the aims of the present invention is to provide a substitute for the best Lewis acid which exhibits less perfluoroalkanesulfonate anion, in particular triflate anion, than tritriflates.

Another aim of the present invention is the sulfonation of both activated and deactivated aromatic substrates under easily employed conditions.

The present invention achieves these objectives and provides a process which makes it possible to overcome the abovementioned disadvantages.

A process for the sulfonation of an aromatic compound has now been found, and it is this which constitutes the subject-matter of the present invention, which consists in reacting said aromatic compound with an aryl sulfonating agent in the presence of a catalyst, characterized in that the sulfonation reaction is carried out in the presence of a catalytically effective amount of a mixture of bismuth trihalide and of perfluoroalkanesulfonic acid.

During the use of the catalyst of the present invention, it may happen that the halide ion is partially displaced by the sulfonic acid and escapes in the form of hydrohalic acid. This displacement only affects at most two thirds of the halides bonded to the bismuth, generally at most ⅓, and a small fraction of ⅓. This is because the displacement of the second and third halides from the bismuth halide is increasingly difficult as the replacement proceeds. A limitation on the amount of perfluoroalkanesulfonic acid with respect to the bismuth is for this reason desirable. This ratio will be specified subsequently. It is certainly preferable to prevent the triperfluorosulfonate from being formed but this restriction and not really one as generally only mono- and diexchanged derivatives are formed.

Although it is preferable to obtain the catalytic mixture by mixing perfluoroalkanesulfonic acid and bismuth halide, said catalytic mixture can be prepared by any mixings, in particular at the time of use, of halide ion, of bismuth cation and of triflate ion in appropriate ratios.

In the present text, the term "perfluoroalkanesulfonic acid" is understood to mean the compounds of formula $R_fSO_3H$. Any $R_f$ group which comprises a perfluoromethylene (—$CF_2$—), preferably a perfluoroethylene (—$CF_2$—$CF_2$—), carrying the sulfonic group is regarded as an $R_f$ group.

More generally, the catalytic mixture according to the present invention is targeted at reactions catalyzed by Lewis acids in which conventional Lewis acids are replaced by the mixture according to the present invention.

In the present text, the term "triflic acid" is understood to mean trifluoromethanesulfonic acid $CF_3SO_3H$.

The present invention is targeted essentially at the bismuth trihalide and perfluoroalkanesulfonic acid mixtures in which the molar ratio is less than the stoichiometry resulting in the complete exchange of the halide by the sulfonic functional group. More specifically, the ratio of the sulfonic functional groups, expressed in equivalents, to the bismuth salts, expressed in moles, is advantageously at most equal to 2, preferably at most equal to 1.5, more preferably at most equal to 1.

More specifically, a subject-matter of the present invention is a process for the sulfonation of an aromatic compound corresponding to the general formula (I):

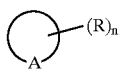
(I)

in which:

A symbolizes the residue of a ring forming all or part of a monocyclic or polycyclic, aromatic, carbocyclic or heterocyclic system, it being possible for said cyclic residue to carry a radical R representing a hydrogen atom or one or more identical or different substituents, n represents the number of substituents on the ring.

The invention applies in particular to the aromatic compounds corresponding to the formula (I) in which A is the residue of a cyclic compound preferably having at least 4 atoms in the optionally substituted ring and representing at least one of the following rings:

a monocyclic or polycyclic aromatic carbocycle, a monocyclic or polycyclic aromatic heterocycle comprising at least one of the heteroatoms O, N and S.

To be more specific, without for all that limiting the scope of the invention, the optionally substituted residue A represents the residue:

1)—of a monocyclic or polycyclic aromatic carbocyclic compound.

The term "polycyclic carbocyclic compound" is understood to mean:

a compound composed of at least 2 aromatic carbocycles which form, with one another, ortho- or ortho- and peri-condensed systems, a compound composed of at least 2 carbocycles, of which only one among them is aromatic, which rings form, with one another, ortho- or ortho- and peri-condensed systems.

2)—of a monocyclic or polycyclic aromatic heterocyclic compound.

The term "polycyclic heterocyclic compound" defines:

a compound composed of at least 2 heterocycles comprising at least one heteroatom in each ring, at least one of the two rings of which is aromatic, which rings form, with one another, ortho- or ortho- and peri-condensed systems, a compound composed of at least one hydrocarbonaceous ring and at least one heterocycle, at least one of the rings of which is aromatic, which rings form, with one another, ortho- or ortho- and peri-condensed systems.

3)—of a compound composed of a sequence of rings as defined in paragraphs 1 and/or 2 bonded to one another:

via a valency bond, via an alkylene or alkylidene radical having from 1 to 4 carbon atoms, preferably a methylene or isopropylidene radical, via one of the following groups:

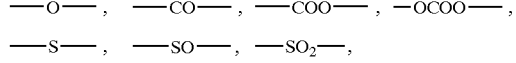

-continued

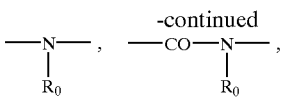

in these formulae, $R_0$ represents a hydrogen atom, an alkyl radical having from 1 to 4 carbon atoms, a cyclohexyl radical or a phenyl radical.

Mention may be made, as examples of rings under 1) to 3), of:

1)—benzene, toluene, xylene, naphthalene or anthracene,

2)—furan, pyrrole, thiofene, isoxazole, furazan, isothiazole, imidazole, pyrazole, pyridine, pyridazine, pyrimidine, quinoline, naphthyridine, benzofuran or indole, 3)—biphenyl, 1,1'-methylenebiphenyl, 1,1'-isopropylidenebiphenyl, 1,1'-oxybiphenyl or 1,1'-iminobiphenyl.

In the process of the invention, use is preferably made of an aromatic compound of formula (I) in which A represents a benzene nucleus.

The aromatic compound of formula (I) can carry one or more substituents.

The number of substituents present on the ring depends on the carbon condensation of the ring and on the presence or absence of unsaturations in the ring.

The maximum number of substituents which can be carried by a ring is easily determined by a person skilled in the art.

In the present text, the term "more" is understood to mean generally less than 4 substituents on an aromatic nucleus. Examples of substituents are given below but this list does not have a limiting nature. As mentioned above, the substituents may or may not activate the aromatic nucleus.

The residue A can optionally carry one or more substituents which are represented in the formula (I) by the symbol R and the preferred meanings of which are defined below: the R radical or radicals represent one of the following groups:

a hydrogen atom, a linear or branched alkyl radical having from 1 to 6 carbon atoms, preferably from 1 to 4 carbon atoms, such as methyl, ethyl, propyl, isopropyl, butyl, isobutyl, sec-butyl or tert-butyl, a linear or branched alkenyl radical having from 2 to 6 carbon atoms, preferably from 2 to 4 carbon atoms, such as vinyl or allyl, a linear or branched alkoxy radical having from 1 to 6 carbon atoms, preferably from 1 to 4 carbon atoms, such as the methoxy, ethoxy, propoxy, isopropoxy or butoxy radicals, a cyclohexyl radical, an acyl group having from 2 to 6 carbon atoms, a radical of formula:

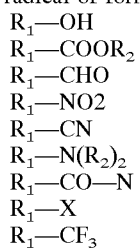

in said formulae, $R_1$ represents a valency bond or a saturated or unsaturated, linear or branched, divalent hydrocarbonaceous radical having from 1 to 6 carbon atoms, such as, for example, methylene, ethylene, propylene, isopropylene or isopropylidene; the radicals $R_2$, which are identical or different, represent a hydrogen atom or a linear or branched alkyl radical having from 1 to 6 carbon atoms; X symbolizes a halogen atom, preferably a chlorine, bromine or fluorine atom.

When n is greater than or equal to 2, two R radicals and the 2 successive atoms of the aromatic ring can be bonded to one another via an alkylene, alkenylene or alkenylidene radical having from 2 to 4 carbon atoms to form a saturated, unsaturated or aromatic heterocycle having from 5 to 7 carbon atoms. One or more carbon atoms can be replaced by another heteroatom, preferably oxygen. Thus, the R radicals can represent a methylenedioxy or ethylenedioxy radical.

The present invention applies very particularly to the aromatic compounds corresponding to the formula (I) in which:

the R radical or radicals represent one of the following groups:

a hydrogen atom, an OH group, a linear or branched alkyl radical having from 1 to 6 carbon atoms, a linear or branched alkenyl radical having from 2 to 6 carbon atoms, a linear or branched alkoxy radical having from 1 to 6 carbon atoms, a —CHO group, an acyl group having from 2 to 6 carbon atoms, a —COOR$_2$ group, where $R_2$ has the meaning given above, an —NO$_2$ group, an —NH$_2$ group, a halogen atom, preferably fluorine, chlorine or bromine, a —CF$_3$ group, n is a number equal to 0, 1, 2 or 3.

Use is more particularly made, among the compounds of formula (I), of those corresponding to the following formulae:

a monocyclic or polycyclic aromatic carbocyclic compound with rings which can form, with one another, an ortho-condensed system corresponding to the formula (Ia):

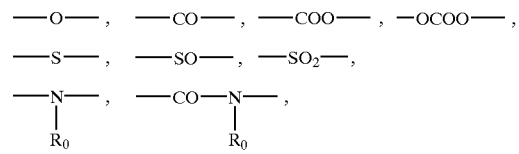

(Ia)

in said formula (Ia), m represents a number equal to 0, 1 or 2 and the symbols R, which are identical or different, and n having the meaning given above, a compound composed of a sequence of two or more monocyclic aromatic carbocycles corresponding to the formula (Ib):

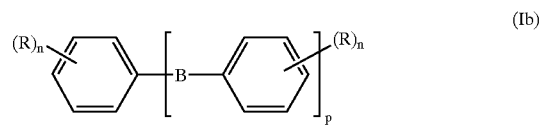

(Ib)

in said formula (Ib), the symbols R, which are identical or different, and n have the meaning given above, p is a number equal to 0, 1, 2 or 3 and B represents:

a valency bond, an alkylene or alkylidene radical having from 1 to 4 carbon atoms, preferably a methylene or isopropylidene radical, one of the following groups:

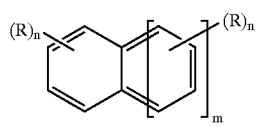

in these formulae, $R_0$ represents a hydrogen atom, an alkyl radical having from 1 to 4 carbon atoms, a cyclohexyl radical or a phenyl radical.

The compounds of formula (I) preferably employed correspond to the formulae (Ia) and (Ib) in which:

R represents a hydrogen atom, a hydroxyl group, a —CHO group, an —NO$_2$ group, an —NH$_2$ group, a linear or branched alkyl or alkoxy radical having from 1 to 6 carbon atoms, preferably from 1 to 4 carbon atoms, or a halogen atom, B symbolizes a valency bond, an alkylene or alkylidene radical having from 1 to 4 carbon atoms or an oxygen atom, m is equal to 0 or 1, n is equal to 0, 1 or 2, p is equal to 0 or 1.

More preferably still, the choice is made of the compounds of formula (I) in which R represents a hydrogen atom, a hydroxyl group, a methyl radical, a methoxy radical or a halogen atom.

Mention may more particularly be made, by way of illustration of compounds corresponding to the formula (I), of:

halogenated or nonhalogenated aromatic compounds, such as benzene, toluene, chlorobenzene, dichlorobenzenes, trichlorobenzenes, fluorobenzene, difluorobenzenes, chlorofluorobenzenes, chlorotoluenes, fluorotoluenes, bromobenzene, dibromobenzenes, bromofluorobenzenes, bromochlorobenzenes, trifluoromethylbenzene, trifluoromethoxybenzene, trichloromethylbenzene, trichloromethoxybenzene or trifluoromethylthiobenzene, aminated or nitrated aromatic compounds, such as aniline and nitrobenzene, phenolic compounds, such as phenol, o-cresol or guaiacol, monoethers, such as anisole, ethoxybenzene (phenetole), butoxybenzene, isobutoxybenzene, 2-chloroanisole, 3-chloroanisole, 2-bromoanisole, 3-bromoanisole, 2-methylanisole, 3-methylanisole, 2-ethylanisole, 3-ethylanisole, 2-isopropylanisole, 3-isopropylanisole, 2-propylanisole, 3-propylanisole, 2-allylanisole, 2-butylanisole, 3-butylanisole, 2-tert-butylanisole, 3-tert-butylanisole, 2-benzylanisole, 2-cyclohexylanisole, 1-bromo-2-ethoxybenzene, 1-bromo-3-ethoxybenzene, 1-chloro-2-ethoxybenzene, 1-chloro-3-ethoxybenzene, 1-ethoxy-2-ethylbenzene, 1-ethoxy-3-ethylbenzene, 2,3-dimethylanisole or 2,5-dimethylanisole, diethers, such as veratrole, 1,3-dimethoxybenzene, 1,2-diethoxybenzene, 1,3-diethoxybenzene, 1,2-dipropoxybenzene, 1,3-dipropoxybenzene, 1,2-methylenedioxybenzene or 1,2-ethylenedioxybenzene, triethers, such as 1,2,3-trimethoxybenzene, 1,3,5-trimethoxybenzene or 1,3,5-triethoxybenzene.

The compounds to which the process according to the invention applies in a more particularly advantageous way are benzene, toluene, phenol, anisole, m-xylene, mesitylene, chlorobenzene or veratrole.

As regards the sulfonating reagent, it corresponds more particularly to the formula (II):

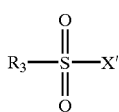

(II)

in which:

R$_3$ represents an aryl radical, such as in particular phenyl or naphthyl, which can optionally be substituted by an organic radical, such as a C$_1$–C$_8$ alkyl or a C$_1$–C$_8$ alkoxy group, a nitro radical or a halogen atom, for example chlorine. It is necessary for this phenyl radical to be more deactivated than the aromatic compound as, in the contrary case, the aryl sulfonating agent itself would be sulfonated.

X' represents a leaving group which can in particular be a sulfonyloxy group carried by a radical with the same definition as R$_3$, advantageously so that the molecule forms a symmetrical anhydride, or preferably a halogen atom, preferably a chlorine or bromine atom.

Mention may more particularly be made, by way of illustration of aryl sulfonating agents corresponding to the formula (II), of:

benzenesulfonyl chloride, 4-methylbenzenesulfonyl chloride, 4-chlorobenzenesulfonyl chloride, p-nitrobenzenesulfonyl chloride, methoxybenzenesulfonyl chlorides, naphthylsulfonyl chlorides.

In accordance with the process of the invention, the sulfonation reaction of an aromatic compound is carried out in the presence of a catalyst which is a mixture of a bismuth trihalide and of perfluoroalkanesulfonic acid.

In accordance with the process of the invention, the reaction between the aromatic compound and the aryl sulfonating agent can be carried out in the presence or in the absence of an organic solvent, it being possible for one of the reactants to be used as reaction solvent.

An alternative form of the process of the invention consists in carrying out the reaction in an organic solvent.

A solvent for the starting substrate is preferably chosen and more preferably a polar aprotic organic solvent.

Mention may more particularly be made, as examples of polar aprotic organic solvents which can also be employed in the process of the invention, of linear or cyclic carboxamides, such as N,N-dimethylacetamide (DMAC), N,N-diethylacetamide, dimethylformamide (DMF), diethylformamide or 1-methyl-2-pyrrolidinone (NMP); nitrated compounds, such as nitromethane, nitroethane, 1-nitropropane, 2-nitropropane or their mixtures, or nitrobenzene; aliphatic or aromatic nitriles, such as acetonitrile, propionitrile, butanenitrile, isobutanenitrile, benzonitrile or benzyl cyanide; dimethyl sulfoxide (DMSO); tetramethyl sulfone (sulfolane), dimethyl sulfone or hexamethylphosphotriamide (HMPT); dimethylethyleneurea, dimethylpropyleneurea or tetramethylurea; or propylene carbonate.

The preferred solvents are: nitromethane, nitroethane, 1-nitropropane or 2-nitropropane.

A mixture of organic solvents can also be used.

In a first stage of the process of the invention, the sulfonation of the aromatic compound is carried out. In a following stage, the hydrolysis of the reaction mass obtained is carried out.

The ratio of the number of moles of aromatic compound to the number of moles of aryl sulfonating agent can vary as the substrate can be used as reaction solvent. Thus, the ratio can range from 0.1 to 10, preferably between 1.0 and 4.0.

The amount of catalyst or catalytic mixture employed is determined so that the ratio of the number of moles of catalyst to the number of moles of aryl sulfonating agent is less than 1.0 and preferably varies between 0.001 and 0.8 and more preferably still between 0.02 and 0.2.

As regards the amount of organic solvent employed, it is generally chosen so that the ratio of the number of moles of organic solvent to the number of moles of aromatic compound preferably varies between 0 and 100 and more preferably still between 0 and 50.

The temperature at which the sulfonation reaction is carried out depends on the reactivity of the starting substrate and on that of the aryl sulfonating agent.

It is between 20° C. and 200° C., preferably between 100° C. and 140° C.

The reaction is generally carried out at atmospheric pressure but lower or higher pressures may also be suitable.

From a practical viewpoint, there are no restrictions regarding the use of the reactants. They can be introduced in any order.

After bringing the reactants in contact, the reaction mixture is brought to the desired temperature.

Another alternative form of the invention consists in heating one of the reactants (aryl sulfonating agent or aromatic compound) with the catalytic mixture and in then introducing the other reactant.

The duration of the reaction depends on numerous parameters. It is generally from 10 minutes to 14 hours.

In a following stage of the process of the invention, a hydrolysis treatment of the reaction mass obtained is carried out.

The amount of water employed can vary very widely. The ratio of the number of moles of water to the number of moles of aromatic compound can vary between 10 and 100 and preferably between 20 and 30.

To this end, a preferred embodiment of this operation consists in adding the reaction mass to a heel of water brought to a temperature of between 0° C. and 100° C., preferably between 15° C. and 30° C.

An alternative form of the invention consists in replacing the water with a basic solution, generally a sodium hydroxide, sodium carbonate or sodium hydrogencarbonate solution, having a concentration of 5 to 20% by weight.

The catalytic mixture, a portion of which is then in the salt form, is separated off, preferably by filtration. This salt can be recycled after drying.

At the end of the reaction, the desired product, namely the aromatic sulfonation [lacuna], is recovered in the organic phase.

The aqueous and organic phases are separated.

The organic phase is washed one or more times, preferably twice, with water.

The aqueous and organic phases are separated.

The sulfonated aromatic product is subsequently recovered from the organic phase according to known techniques, by removing the organic solvent, by distillation or by crystallization.

Another alternative form of the invention consists in recovering the sulfonated aromatic product directly by distillation of the organic phase comprising the latter and the catalyst.

In accordance with the process of the invention, an aromatic sulfonation product is obtained which can be represented by the formula (III):

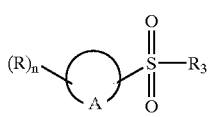
(III)

in said formula (III), A, R, $R_3$ and n have the meaning given above.

According to an alternative form of the process of the present invention, the catalytic mixture can be prepared beforehand, before the addition of the aromatic compound and of the aryl sulfonating agent.

The catalytic mixture is advantageously prepared according to a process which consists in mixing, at low temperature, a bismuth trihalide and the perfluoroalkanesulfonic acid.

As indicated above, the present invention is essentially targeted, as catalyst of Lewis acid type, at bismuth trihalide and perfluoroalkanesulfonic acid mixtures for which the ratio is less than the stoichiometry resulting in the complete exchange of the halide by the sulfonic functional group, that is to say, in the case of acids carrying a single sulfonic functional group, a ratio of less than 3. Thus, more specifically, the ratio of the sulfonic functional groups, expressed in equivalents, to the bismuth salts, expressed in moles, ($R_fSO_3^-$/Bi ratio) is generally at most equal to 2.5, advantageously at most equal to 2, preferably at most equal to 1.5 and, for economical reasons, more preferably at most equal to 1. It is desirable for said ratio to be at least equal to 0.1, advantageously to 0.5, preferably to 1.

Depending on the amount of triflic acid employed, a catalyst will be obtained thus comprising more or less triflate anions.

The reaction for preparing the catalyst can be carried out in an organic solvent.

Recourse is more particularly had to halogenated aliphatic hydrocarbons, preferably to dichloromethane, chloroform, carbon tetrachloride or 1,2-dichloroethane.

According to a preferred embodiment, the perfluoroalkanesulfonic acid is gradually added to the mixture comprising the bismuth trihalide and the organic solvent.

As regards the reaction temperature, it is advantageously chosen at less than 0° C. and more preferably between −100° C. and −20° C.

At the end of the reaction, the reaction mixture is allowed to return to room temperature (preferably between 15° C. and 25° C.) and bismuth triflate is obtained.

Said precipitate is separated according to conventional solid/liquid separation techniques, preferably by filtration.

The catalyst thus prepared is employed in the sulfonation process according to the invention.

The catalyst which has been used for the sulfonylation reactions can also be used as acylation or alkylation catalyst involving reactions similar to Friedel-Craft's reactions (intermediacy of a cation, in particular a carbocation, especially an acylium). When a perfluoroalkanesulfonic acid distinct from triflic acid is used, it is preferable for this acid to have at most 15 carbon atoms, preferably at most 10. In addition, for reasons of solubility in an organic medium, it is particularly advantageous for the radical connected to the sulfur of the sulfonic functional group to be completely perfluorinated, that is to say for all the hydrogens of the alkane to be replaced by fluorines.

The examples which follow illustrate the invention without, however, limiting it.

In the examples, the yields mentioned correspond to the following definition:

$$\text{Yield} = \frac{\text{number of moles of [lacuna] of aromatic sulfonation formed}}{\text{number of moles of minor reactant}} \%$$

The term "minor reactant" is understood to mean either the aromatic substrate or the aryl sulfonating agent, depending on the relative amounts of each introduced.

EXAMPLE 1 to 17

Example 1

Sulfonation of Anisole in the Presence of Bismuth Triflate

The procedure which is used in Examples 2 to 17 is defined below.

The bismuth halide $BiCl_3$ (197 mg, 0.625 mmol), mesitylene (3 g, 24.96 mmol), benzensulfonyl chloride (2.2 g, 12.48 ml) and triflic acid (187 mg, 1.25 mmol) are introduced into a 50 ml round-bottom flask purged with argon which is equipped with a reflux condenser provided with a calcium chloride drying tube.

10 mmol of mesitylene substrate and 5 mmol of aryl sulfonating agent are employed for a molar ratio of 2.

The catalyst is introduced in a proportion of 5 molar % with respect to the substrate.

The mixture is brought, using an oil bath, to the reaction temperature of 120° C., also mentioned in the summarizing Table I below, for 1 h.

After cooling, 20 ml of a saturated $NaHCO_3$ solution are added and the products obtained are extracted with $CH_2Cl_2$ (2×20 ml).

After drying and evaporating the organic phase and recrystallizing the solid product from ethanol, 2.82 g (87% yield) of (2,4,6-trimethylphenyl) phenyl sulfone are obtained (M.p.: 81° C.).

EXAMPLE 2–17

The procedure of Example 1 is repeated exactly, the reactants and the catalyst optionally being changed. The conditions and results are recorded in Table I below.

TABLE I

| Ref. Ex. | Aryl sulfonating agent | Substrate[a] | Catalyst | Temperature[b] °C | Duration h | Yield (%) [o:m:p] |
|---|---|---|---|---|---|---|
| 1 | PhSO₂Cl | anisole | A | 120 | 0.5 | 82 [47:0:53][e] |
| 2 | PhSO₂Cl | anisole | B | 120 | 0.5 | trace |
| 3 | PhSO₂Cl | anisole | C | 120 | 0.5 | 4 |
| 4 | PhSO₂Cl | mesitylene | A | 120 | 1 | 95[f] |
| 5 | PhSO₂Cl | mesitylene | B | 120 | 1 | 8 |
| 6 | PhSO₂Cl | m-xylene | A | 120 | 1 | 93[g] |
| 7 | PhSO₂Cl | m-xylene | B | 120 | 1 | 14 |
| 8 | PhSO₂Cl | toluene | A | 120 | 1.25 | 95 [39:6:55][k] |
| 9 | PhSO₂Cl | toluene | B | 120 | 1.25 | trace |
| 10 | PhSO₂Cl | benzene | A | 80 | 12 | 65[i] |
| 11 | PhSO₂Cl | benzene | B | 80 | 12 | 7 |
| 12 | PhSO₂Cl | chlorobenzene | A | 120 | 4 | 70 [3:0:97][j] |
| 13 | PhSO₂Cl | chlorobenzene | B | 120 | 4 | 28 [3:0:97] |
| 14 | 4-Me-C₆H₄SO₂Cl | toluene | A | 120 | 1.25 | 97 [29:5:66][k] |
| 15 | 4-Me-C₆H₄SO₂Cl | toluene | B | 120 | 1.25 | 25 [29:5:66] |
| 16 | 4-Cl-C₆H₄SO₂Cl | toluene | A | 120 | 1.25 | 95 [42:7:51][l] |
| 17 | 4-Cl-C₆H₄SO₂Cl | toluene | B | 120 | 1.25 | 4 |

[a]ArH/Ar'SO₂Cl = 2/1;
[b]temperature of the oil bath;
[c]catalyst: A:BiCl₃ (5 mol %) + TfOH (10 mol %), B: TfOH 10 mol %), C: BiCl₃ (5 mol %);
[d]by GC using tetradecane as internal standard;
[e](methoxyphenyl) phenyl sulfone, accompanied by 15% of phenyl benzenesulfonate;
[f](2,4,6-trimethylphenyl) phenyl sulfone;
[g](2,4-dimethylphenyl) phenyl sulfone, accompanied by 3% of (2,6-dimethylphenyl) phenyl sulfone;
[h]phenyl tolyl sulfone;
[i]diphenyl sulfone;
[j](chlorophenyl) phenyl sulfone;
[k]ditolyl sulfone;
[l](4-chlorophenyl) tolyl sulfone.

What is claimed is:

1. A process for the sulfonation of an aromatic compound corresponding to the general formula (I):

(I)

wherein:
A symbolizes a ring forming a monocyclic or polycyclic aromatic carbocyclic compound or a monocyclic or polycyclic aromatic heterocyclic compound, said ring optionally bearing a radical R, which represent one of the following groups:
a hydrogen atom,
a linear or branched alkyl radical having from 1 to 6 carbon atoms,
a linear or branched alkenyl radical having from 2 to 6 carbon atoms,
a linear or branched alkoxy radical having from 1 to 6 carbon atoms,
a cyclohexyl radical,
an acyl group having from 2 to 6 carbon atoms, or
a radical of formula:
R₁—OH
R₁—COOR₂
R₁—CHO
R₁—NO₂
R₁—CN
R₁—C(O)—(NR₂)₂
R₁—X, or
R₁—CF₃
wherein, R₁ represents a valency bond or a saturated or unsaturated, linear or branched, divalent hydrocarbon radical having from 1 to 6 carbon atoms; the radicals R₂, which are identical or different, represent a hydrogen atom or a linear or branched alkyl radical having from 1 to 6 carbon atoms; X symbolizes a halogen atom;
n represents the number of substituents on the ring, said process comprising the steps of:
a) reacting said aromatic compound with a sulfonating agent, in the presence of a catalytically effective amount of a catalyst which is a mixture of bismuth trihalide and of perfluoroalkanesulfonic acid, whith a molar ratio less than the stoichiometry resulting in the complete exchange of the halide by the sulfonic functional group, to obtain a sulfonated aromatic compound, and
b) recovering the sulfonated aromatic compound obtained in step a).

2. A process for the sulfonation of an aromatic compound according to claim 1, wherein the sulfonating agent is an aryl or alkyl sulfonating agent.

3. A process according to claim 1, wherein the R radical or radicals represent methyl, ethyl, propyl, isopropyl, butyl, isobutyl, sec-butyl, tert-butyl, vinyl, allyl, methoxy, ethoxy, propoxy, isopropoxy or butoxy radicals, R₁ represents methylene, ethylene, propylene, isopropylene or isopropylidene; and X is a chlorine, bromine or fluorine atom.

4. A process according to claim 1, wherein, when n is greater than or equal to 2, two R radicals and the 2 successive atoms of the aromatic ring can be bonded to one another via an alkylene, alkenylene or alkenylidene radical having from 2 to 4 carbon atoms to form a saturated, unsaturated or aromatic heterocycle having from 5 to 7 carbon atoms, optionally one or more carbon atoms is replaced by oxygen.

5. A process according to claim 1, wherein the R radical or radicals represent:
a hydrogen atom,
an OH group,
a linear or branched alkyl radical having from 1 to 6 carbon atoms,
a linear or branched alkenyl radical having from 2 to 6 carbon atoms,
a linear or branched alkoxy radical having from 1 to 6 carbon atoms,
a —CHO group,
an acyl group having from 2 to 6 carbon atoms,
a —COOR₂ group, where R₂ has the meaning given above,
an —NO₂ group,
an —NH₂ group,
a halogen atom, or
a —CF₃ group, and
n is a number equal to 1, 2 or 3.

6. A process according to claim 1, wherein the aromatic compound corresponding to the general formula (I) is a monocyclic or polycyclic aromatic carbocyclic compound with rings which can form, with one another, an ortho-condensed system corresponding to the formula (Ia):

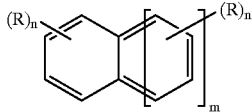

in said formula (Ia), in represents a number equal to 0, 1 or 2 and the symbols, which are identical or different, and n have the meaning set forth for formula (I), and n having the meaning given above.

7. A process according to 1, wherein the aromatic compound corresponding to the general formula (I) is a compound composed of a sequence of two or more monocyclic aromatic carbocycles corresponding to the formula (Ib):

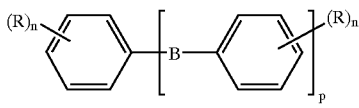

in said formula (Ib), the symbols R, which are identical or different, and n have the meaning set forth for formula (I), p is a number equal to 0, 1, 2 or 3 and B represents:

a valency bond, an alkylene or alkylidene radical having from 1 to 4 carbon atoms, or one of the following groups:

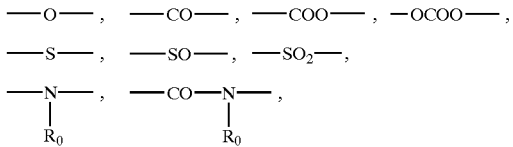

in these formulae, $R_0$ represents a hydrogen atom, an alkyl radical having from 1 to 4 carbon atoms, a cyclohexyl radical or a phenyl radical.

8. A process according to claim 6, wherein the aromatic compound corresponds to the formula (Ia) or (Ib) wherein:

R represents a hydrogen atom, a hydroxyl group, a —CHO group, an —$N_2$ group, an —$NH_2$ group, a linear or branched alkyl or alkoxy radical having from 1 to 6 carbon atoms, B symbolizes a valency bond, an alkylene or alkylidene radical having from 1 to 4 carbon atoms or an oxygen atom, m is equal to 0 or 1, n is equal to 0, 1 or 2, and p is equal to 0 or 1.

9. A process according to 1, wherein the aromatic compound corresponds to the general formula (I) wherein R represents a hydrogen atom, a hydroxyl group, a methyl radical, a methoxy radical or a halogen atom.

10. A process according to claim 1, wherein the aromatic compound is benzene, toluene, phenol, anisole, m-xylene, mesitylene, chlorobenzene or veratrole.

11. A process according to claim 1, wherein the aryl sulfonating agent corresponds to the formula (II):

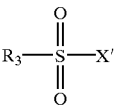

wherein:

$R_3$ represents an aryl radical, optionally substituted by an organic radical, a nitro radical or a halogen atom, with the proviso that this phenyl radical is more deactivated than the aromatic compound of formula (I), and X' represents a halogen atom.

12. A process according to claim 11, wherein the aryl sulfonating agent is:

benzenesulfonyl chloride, 4-methylbenzenesulfonyl chloride, 4-chlorobenzenesulfonyl chloride, p-nitrobenzenesulfonyl chloride, methoxybenzenesulfonyl chloride, or naphthylsulfonyl chloride.

13. A process according to claim 1, wherein in step a), a polar aprotic organic solvent is used.

14. A process according to claim 13, wherein the organic solvent is N,N-dimethylacetamide (DMAC), N,N-diethylacetamide, dimethylformamide (DMF), diethylformamide, 1-methyl-2-pyrrolidinone (NMP), nitromethane, nitroethane, 1-nitropropane, 2-nitropropane, nitrobenzene, acetonitrile, propionitrile, butanenitrile, isobutanenitrile, benzonitrile, benzyl cyanide, dimethyl sulfoxide (DMSO), tetramethyl sulfone (sulfolane), dimethyl sulfone, hexamethylphosphotriamide (HMPT), dimethylethyleneurea, dimethylpropyleneurea, tetramethylurea; or propylene carbonate.

15. A process according to claim 1, wherein step a) is carried out with a ratio of number of moles of aromatic compound to number of moles of aryl sulfonating agent of between 0.1 and 10.

16. A process according to claim 15, wherein the ratio is between 1.0 and 4.0.

17. A process according to claim 15, wherein in step a), the catalyst is used in an amount such that the ratio of moles of catalyst to the moles of aryl sulfonating agent is between 0.001 and 0.8.

18. A process according to claim 16, wherein said ratio is between 0.02 and 0.2.

19. A process according to claim 1, wherein step a) is carried out at a temperature of between 20° C. and 200° C.

20. A process according to claim 1, wherein step a) is carried out in a ratio: perfluoroalkanesulfonic functional groups, expressed in equivalents of sulfonic acid, to bismuth trihalide, expressed in moles, less than stoichiometry resulting in a complete exchange of the halide by the sulfonic functional group.

21. A process according to claim 20, wherein said ratio is at most equal to 2.

22. A process according to claim 21, wherein said ratio is at most equal to 1.

* * * * *